United States Patent
Benam et al.

(10) Patent No.: US 11,499,128 B2
(45) Date of Patent: Nov. 15, 2022

(54) ORGAN-ON-CHIP MICROPHYSIOLOGICAL SYSTEM

(71) Applicant: THE REGENTS OF THE UNIVERSITY OF COLORADO, Denver, CO (US)

(72) Inventors: Kambez Hajipouran Benam, Denver, CO (US); Alex Kaiser, Keenesburg, CO (US)

(73) Assignee: The Regents of the University of Colorado, Denver, CO (US)

(*) Notice: Subject to any disclaimer, the term of this patent is extended or adjusted under 35 U.S.C. 154(b) by 118 days.

(21) Appl. No.: 16/648,854

(22) PCT Filed: Sep. 21, 2018

(86) PCT No.: PCT/US2018/052166
§ 371 (c)(1),
(2) Date: Mar. 19, 2020

(87) PCT Pub. No.: WO2019/060680
PCT Pub. Date: Mar. 28, 2019

(65) Prior Publication Data
US 2020/0270558 A1 Aug. 27, 2020

Related U.S. Application Data

(60) Provisional application No. 62/562,216, filed on Sep. 22, 2017.

(51) Int. Cl.
C12M 3/06 (2006.01)
C12M 1/12 (2006.01)
C12M 1/42 (2006.01)

(52) U.S. Cl.
CPC ............ *C12M 23/16* (2013.01); *C12M 25/14* (2013.01); *C12M 35/08* (2013.01)

(58) Field of Classification Search
CPC ...... C12M 23/16; C12M 25/14; C12M 35/08; A61B 17/435; A61D 19/04;
(Continued)

(56) References Cited

U.S. PATENT DOCUMENTS

| 4,649,911 A | 3/1987 | Knight et al. |
| 8,281,641 B1 | 10/2012 | Wooten et al. |

(Continued)

FOREIGN PATENT DOCUMENTS

| CN | 106635954 | 5/2017 |
| WO | 2007119073 | 10/2007 |

(Continued)

OTHER PUBLICATIONS

Huh, D et al. "From Three-Dimensional Cell Culture to Organs-on-Chips" Trends Cell Biology, Dec. 7, 2011; vol. 21 Issue 12: pp. 745—754.doi:10.1016/j.tcb.2011.09.005.
(Continued)

*Primary Examiner* — Michael L Hobbs
(74) *Attorney, Agent, or Firm* — Snell & Wilmer L.L.P.

(57) ABSTRACT

An organ-on-chip apparatus includes a first fluid channel, a second fluid channel, and an interface. Respective portions of the first fluid channel and the second fluid channel may extend parallel to and adjacent each other, and the interface may be disposed between the respective portions of the first fluid channel and the second fluid channel such that fluid exchange between the first fluid channel and the second fluid channel is via the interface. The first and second fluid channels may be defined in an extracellular matrix material.

13 Claims, 5 Drawing Sheets

(58) Field of Classification Search
CPC ....... B01L 3/502761; B01L 2200/0668; B01L 2300/0887; B01L 2300/0674; B01L 2300/0816; B01L 2300/0864
See application file for complete search history.

(56) References Cited

U.S. PATENT DOCUMENTS

| | | | |
|---|---|---|---|
| 8,647,410 | B2 | 2/2014 | Borenstein et al. |
| 8,647,861 | B2 | 2/2014 | Ingber et al. |
| 2006/0156978 | A1 | 7/2006 | Lipson et al. |
| 2006/0195179 | A1 | 8/2006 | Sun et al. |
| 2011/0033887 | A1 | 2/2011 | Fang et al. |
| 2011/0086382 | A1 | 4/2011 | Marx |
| 2011/0250585 | A1* | 10/2011 | Ingber .................. C12N 5/0623 435/5 |
| 2011/0250688 | A1 | 10/2011 | Hasan |
| 2014/0057311 | A1* | 2/2014 | Kamm et al. ...... G01N 33/5011 435/29 |
| 2014/0158233 | A1 | 6/2014 | Leslie et al. |
| 2014/0335496 | A1 | 11/2014 | Grego et al. |
| 2014/0342445 | A1 | 11/2014 | Ingber et al. |
| 2014/0352689 | A1 | 12/2014 | Seshadri et al. |
| 2015/0004077 | A1 | 1/2015 | Wikswo et al. |
| 2015/0240194 | A1 | 8/2015 | Neumann et al. |
| 2015/0377861 | A1 | 12/2015 | Pant et al. |
| 2016/0068793 | A1 | 3/2016 | Maggiore |
| 2016/0074558 | A1 | 3/2016 | Murphy et al. |
| 2016/0167051 | A1* | 6/2016 | Collins .............. G01N 15/1056 435/325 |
| 2016/0313306 | A1 | 10/2016 | Ingber et al. |
| 2017/0198252 | A1 | 7/2017 | Mironov et al. |
| 2017/0355153 | A1 | 12/2017 | Albert et al. |
| 2017/0355940 | A1* | 12/2017 | Neumann ............ C12N 5/0697 |
| 2018/0085493 | A1 | 3/2018 | Lee |
| 2018/0106784 | A1 | 4/2018 | Sears et al. |
| 2018/0110901 | A1 | 4/2018 | Lewis |
| 2018/0326665 | A1 | 11/2018 | Gatenholm |

FOREIGN PATENT DOCUMENTS

| | | | |
|---|---|---|---|
| WO | 2012154834 | 11/2012 | |
| WO | 2013086486 | 6/2013 | |
| WO | 2013086502 | 6/2013 | |
| WO | 2013155513 | 10/2013 | |
| WO | 2015138034 | 9/2015 | |
| WO | WO-2015138034 A2 * | 9/2015 | ............ C12M 23/16 |
| WO | 2016164566 | 10/2016 | |
| WO | 2016179242 | 11/2016 | |
| WO | 2017019778 | 2/2017 | |
| WO | 2017040675 | 3/2017 | |

OTHER PUBLICATIONS

Non-Final Office Action dated Mar. 25, 2021 in U.S. Appl. No. 16/438,092.
Final Office Action dated Dec. 17, 2021 in U.S. Appl. No. 16/438,092.
Advisory Action dated Mar. 11, 2022 in U.S. Appl. No. 16/438,092.
Non-Final Office Action dated Oct. 15, 2021 in U.S. Appl. No. 16/648,854.
Final Office Action dated Feb. 25, 2022 in U.S. Appl. No. 16/648,854.
Advisory Action dated May 2, 2022 in U.S. Appl. No. 16/648,854.
Non-Final Office Action dated Jun. 14, 2022 in U.S. Appl. No. 16/648,854.
PCT; International Search Report and Written Opinion dated Dec. 12, 2018 in Application No. PCT/US2018/052166.
PCT; International Preliminary Report on Patentability dated Mar. 24, 2020 in Application No. PCT/US2018/052166.
Non-Final Office Action dated Mar. 16, 2022 in U.S. Appl. No. 16/967,395.
PCT; International Search Report and Written Opinion dated Apr. 15, 2019 in Application No. PCT/US2019/017540.
PCT; International Preliminary Report on Patentability dated Aug. 11, 2020 in Application No. PCT/US2019/017540.
Ozbolat et al., "Bioprinting toward organ fabrication: challenges and future trends," IEEE Transactions on Biomedical Engineering, vol. 60, 3, pp. 691-699 (2013).
Bajaj et al. "3D biofabrication strategies for tissue engineering and regenerative medicine," Annual Review Biomed Engineering, pp. 247-276 (2014).
Landers et al., "Fabrication of soft tissue engineering scaffolds by means of rapid prototyping techniques," Journal of Materials Science, 37, pp. 3107-3116 (2002).
Melchels et al., "Additive manufacturing of tissues and organs," School of Engineering & Physical Sciences, Institute of Biological Chemistry, Biophysics.
Gesim Bioinstruments and Microfluids. https://gesim-bioinstruments-microfluidics.com/. Accessed on: Aug. 4, 2020.
There's Only One 3D-Bioplotter. https://envisiontec.com/3d-printers/3d-bioplotter/. Accessed on: Aug. 4, 2020.
Bioprinter Fabion. https://bioprinting.ru/en/products-services/fabion/. Accessed on: Aug. 4, 2020.
Cyfuse Regenova. https://www.cyfusebio.com/en/product/3dprinter/device/. Accessed on: Aug. 4, 2020.
Cyfuse S-Pike. https://www.cyfusebio.com/en/product/3dprinter/spike/. Accessed on: Aug. 4, 2020.
Aspect Biosystems. https://www.aspectbiosystems.com/technology. Accessed on: Aug. 4, 2020.
BioAssemblybot. https://www.advancedsolutions.com/bioassemblybot. Accessed on: Aug. 4, 2020.
Organovo Technology Platform. https://organovo.com/technology-platform/. Accessed on: Aug. 4, 2020.
Regenhu Biosystem Architects—3DDiscovery Evolution. https://www.regenhu.com/3d-bioprinters. Accessed on: Aug. 4, 2020.
BioBotBasic. https://www.advancedsolutions.com/biobot. Accessed on: Aug. 4, 2020.
Allevi—Compare Bioprinters. https://www.allevi3d.com/compare/. Accessed on: Aug. 4, 2020.
Aether. https://discoveraether.com/. Accessed on: Aug. 4, 2020.
Cellink Life Sciences. https://www.cellink.com/. Accessed on: Aug. 4, 2020.

* cited by examiner

ORGAN-ON-CHIP MICROPHYSIOLOGICAL SYSTEM

CROSS REFERENCE TO RELATED APPLICATIONS

This application is a U.S. national stage entry under 35 U.S.C. § 371 of International Application No. PCT/US2018/052166 filed Sep. 21, 2018 entitled "ORGAN-ON-CHIP MICROPHYSIOLOGICAL SYSTEM," which claims priority to, and the benefit of, U.S. Provisional Patent Application Ser. No. 62/562,216, filed on Sep. 22, 2017, the entire contents of which are incorporated herein by reference in their entirety.

FIELD

The present disclosure relates to biomimetic and microfluidic devices, and more specifically to organ-on-chip devices.

BACKGROUND

Organ-on-chips are biomimetic, microfluidic, cell culture devices created with microchip manufacturing methods that contain continuously perfused hollow microchannels inhabited by living tissue cells arranged to simulate organ-level physiology. By recapitulating the multicellular architectures, tissue-tissue interfaces, chemical gradients, mechanical cues, and vascular perfusion of the body, these devices produce levels of tissue and organ functionality not possible with conventional 2D or 3D culture systems. They also enable high-resolution, real-time imaging and in vitro analysis of biochemical, genetic and metabolic activities of living human cells in a functional human tissue and organ context.

SUMMARY

In various embodiments, the present disclosure provides an organ-on-chip apparatus that includes a first fluid channel, a second fluid channel, and an interface. Respective portions of the first fluid channel and the second fluid channel may extend parallel to and adjacent each other, and the interface may be disposed between the respective portions of the first fluid channel and the second fluid channel such that fluid exchange between the first fluid channel and the second fluid channel is via the interface. The first and second fluid channels may be defined in an extracellular matrix material.

In various embodiments, the first fluid channel is an airway lumen and the second fluid channel is a vascular microchannel. Accordingly, the airway lumen may include at least one of alveolar, bronchiolar, bronchial tracheal, and nasal epithelial cells, with a gaseous fluid, such as air or an aerosol, being configured to flow through the airway lumen. The vascular microchannel may include at least one of microvascular and lymphatic endothelial cells, wherein a liquid fluid is configured to flow through the vascular microchannel. In various embodiments, the interface comprises at least one of a membrane and a porous structure. The at least one of the membrane and the porous structure may have pores having a diameter between about 3 micrometers and 5 micrometers. In various embodiments, the airway lumen has a circular cross-sectional shape.

In various embodiments, a first diameter of the airway lumen is about 30% greater than a second diameter of the vascular microchannel. In various embodiments, opposing sidewalls of the airway lumen proximate the interface comprise inflection locations where curvature of the cross-sectional shape of the airway lumen changes from concave inward to concave outward. These transition sections of the airway lumen may be situated between the inflection locations and the interface, and these transition sections may be concave outward, thus having respective centers of curvature that are outside the airway lumen.

In various embodiments, a smallest distance between transition sections of the airway lumen is a neck diameter of the airway lumen. The neck diameter may be less than a span of the interface in a direction parallel to the neck diameter. In various embodiments, a first diameter of the airway lumen is greater than the span of the interface and a second diameter of the vascular microchannel is equal to the span of the interface. In various embodiments, a radius of curvature of the transition sections of the airway lumen is ⅕ of the span of the interface.

In various embodiments, the first fluid channel comprises a first inlet, a first inlet section, a first body section, a first outlet section, and a first outlet. Correspondingly, the second fluid channel may have a second inlet, a second inlet section, a second body section, a second outlet section, and a second outlet. In various embodiments, the first inlet section and the second inlet section have a same longitudinal length. In various embodiments, the first outlet section and the second outlet section also have the same longitudinal length. Further, in various embodiments, a uniform angle may be defined between the following: the first inlet section and a first beginning portion of the first body section, a first ending portion of the first body section and the first outlet section, the second outlet section and a second beginning portion of the second body section, and a second ending portion of the second body section and the second outlet section. This uniform angle, according to various embodiments, is about 135 degrees.

Also disclosed herein, according to various embodiments, is a method of manufacturing an organ-on-chip apparatus. The method may include defining a first fluid channel and a second fluid channel in an extracellular matrix hydrogel, lining the second fluid channel with endothelial cells to mimic a blood vessel, and lining the first fluid channel with epithelial cells to mimic an airway.

The forgoing features and elements may be combined in various combinations without exclusivity, unless expressly indicated herein otherwise. These features and elements as well as the operation of the disclosed embodiments will become more apparent in light of the following description and accompanying drawings.

Figure 1:
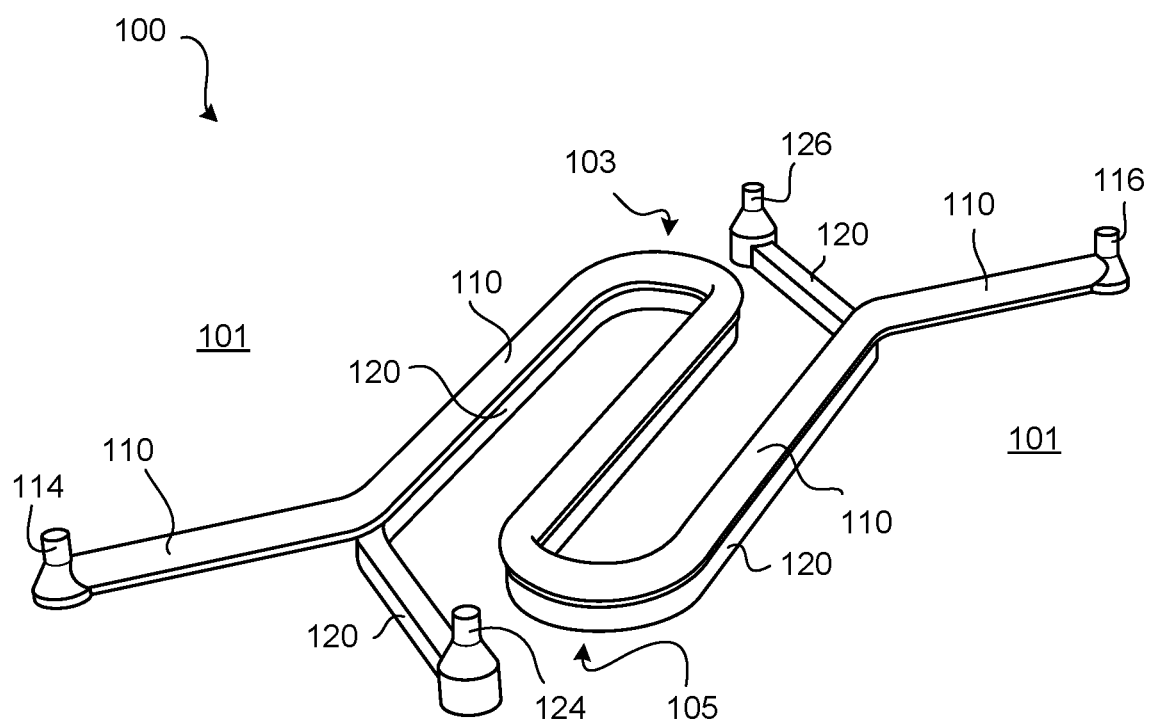
FIG. 1 is a perspective view of an organ-on-chip apparatus, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not of limitation.

In various embodiments, and with reference to FIG. 1, an organ-on-chip apparatus 100 is provided. The apparatus 100 includes a first fluid channel 110, a second fluid channel 120, and an interface 130 (FIGS. 3A and 3B), according to various embodiments. Generally, respective portions of the first fluid channel 110 and the second fluid channel 120 extend parallel to and adjacent each other, with operable fluid exchange between the first fluid channel 110 and the second fluid channel 120 occurring via the interface 130. Additional details pertaining to the channels 110, 120 and the interface 130 are included below with reference to FIGS. 3A, 3B, 4, and 5. In various embodiments, the first fluid channel 110 and the second fluid channel 120 are defined in an extracellular matrix material 101, such as a hydrogel material. Additional details pertaining to the method of manufacturing the apparatus 100 are included below with reference to FIG. 6.

Generally, the organ-on-chip apparatus 100 provided herein is configured to produce organ functionality that provides high-resolution, real-time imaging and in vitro analysis of biochemical, genetic and metabolic activities of living human cells in a functional human tissue and organ context. In various embodiments, the organ-on-chip apparatus 100 is configured to recapitulate multicellular architectures, tissue-tissue interfaces, chemical gradients, mechanical cues, and vascular perfusion of the body. Accordingly, the first and second fluid channels 110, 120 may be inhabited by living tissue cells arranged to simulate organ-level physiology.

For example, the side of the interface 130 facing the first fluid channel 110 may be seeded with alveolar epithelial cells to mimic an epithelial layer while the opposite side of the interface 130 may be seeded with lung microvascular endothelial cells to mimic capillary vessels. That is, the first fluid channel 110 may be an airway lumen and the second fluid channel 120 may be a vascular microchannel. Thus, the organ-on-chip apparatus 100 may be used to mimic an alveolar-capillary unit or conducting airway mucosa, which play vital roles in the maintenance of normal physiological function of the lung as well as in the pathogenesis and progression of various pulmonary diseases. In various embodiments, a gaseous fluid, e.g., air and/or aerosol, can flow through the first fluid channel 110 (e.g., the airway lumen), in which the alveolar, bronchiolar, bronchial tracheal or nasal epithelial cells reside, while a liquid fluid, such as a culture medium, a buffered solution, and/or blood, can flow through the second fluid channel 120 (e.g., vascular microchannel) in which the microvascular or lymphatic endothelial cells reside. In various embodiments, the first fluid channel 110 has a first inlet 114 and a first outlet 116 and the second fluid channel 120 has a second inlet 124 and a second outlet 126.

Figure 2:
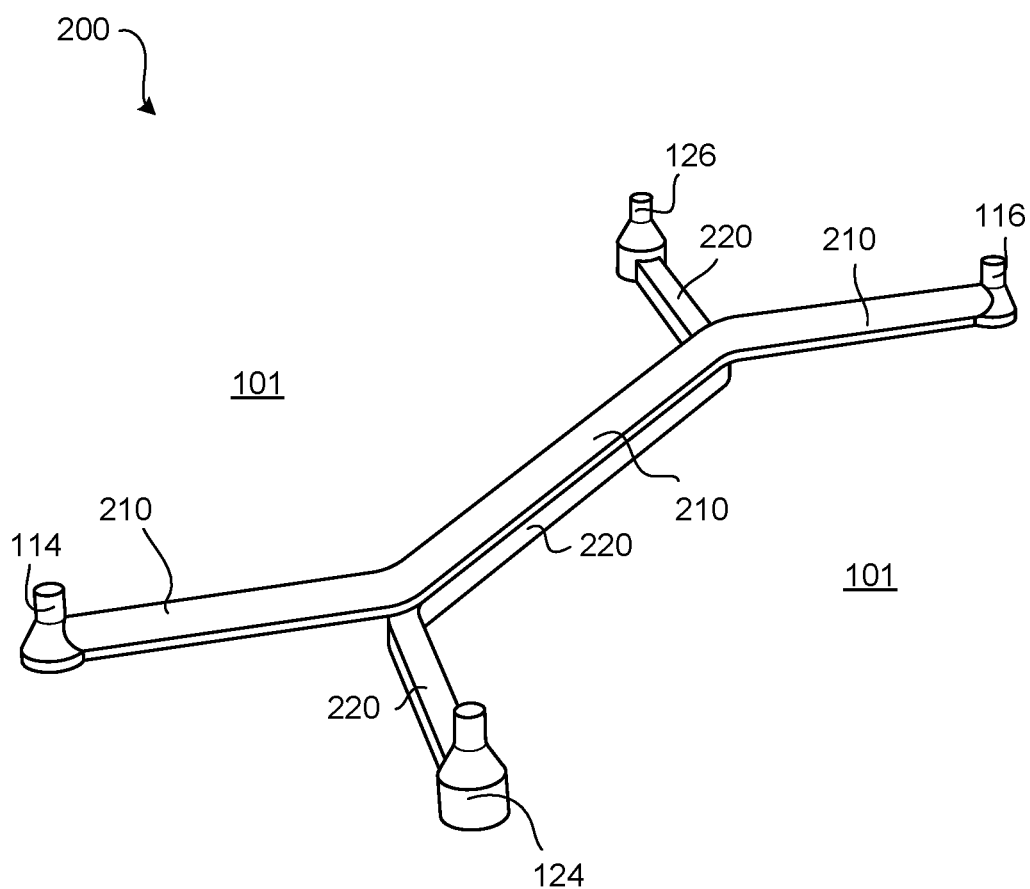
FIG. 2 is a perspective view of an organ-on-chip apparatus, in accordance with various embodiments.

The first and second fluid channels may have various longitudinal shapes. For example, FIG. 1 shows how the overlapping portions of the first and second fluid channels 110, 120 have multiple bends 103, 105, while FIG. 2 shows how the overlapping portion of the first fluid channel 210 and the second fluid channel 220 may be substantially straight (e.g., no bends or curves, etc.). Accordingly, a longitudinal axis (i.e., a longitudinal shape) of the first and second fluid channels may be linear or non-linear. In various embodiments, for example, the longitudinal axis of the first and second fluid channels may be curved, s-shaped, zig-zag shaped, tortuous, branched, forked, and/or bifurcated. In various embodiments, the non-linear longitudinal shape of first and second fluid channels may enable and improve the efficiency, effectiveness, and achievability of various organ functionality analyses. In various embodiments, the length of the longitudinal axis, and thus the functional length of the respective fluid pathways, may be greater than 50 millimeters. In various embodiments, the length of the longitudinal axis may be greater than conventional microdevices, thus increasing the surface coverage of the relevant tissue/cells, thus enabling and improving the efficiency, effectiveness, and achievability of various organ functionality analyses.

Figure 3A:
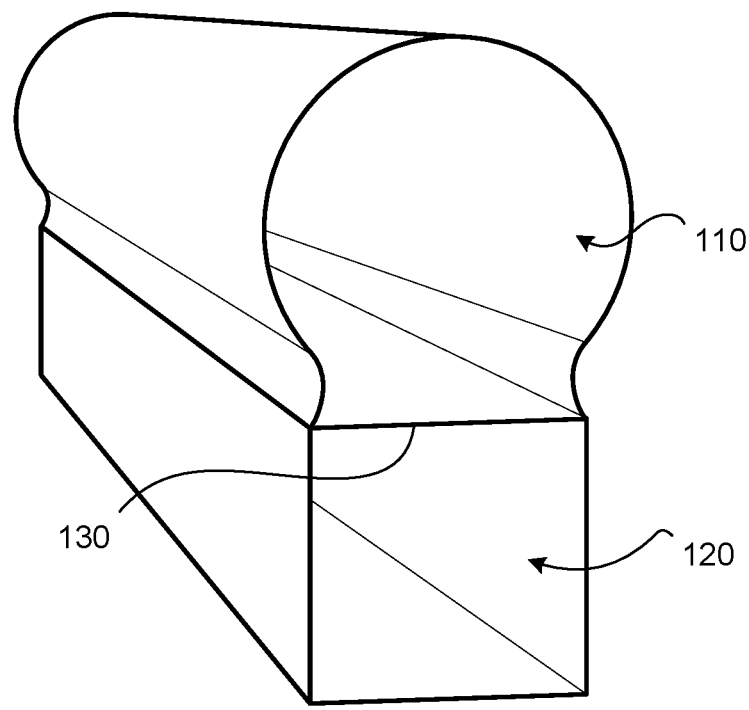
FIG. 3A is a perspective cross-sectional view of a first fluid channel and a second fluid channel of an organ-on-chip apparatus, in accordance with various embodiments.
Figure 3B:
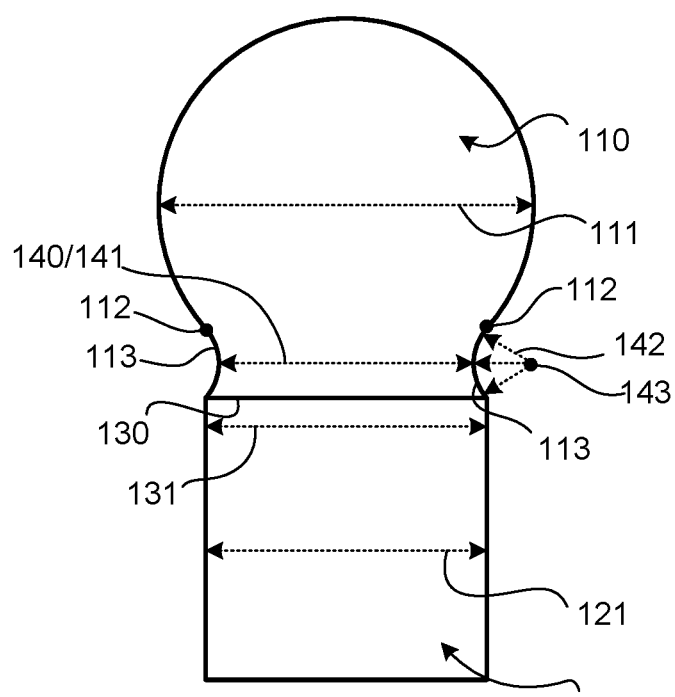
FIG. 3B is a cross-sectional view of a first fluid channel and a second fluid channel of an organ-on-chip apparatus, in accordance with various embodiments.

In various embodiments, and with reference to FIGS. 3A and 3B, the first fluid channel 110 (e.g., the airway lumen), has a circular cross-sectional shape. As used herein, the term "circular cross-sectional shape" refers to a rounded, non-rectangular shape. That is, the cross-sectional shape of the first fluid channel 110 may be elliptical, oval, obround, etc. The circular cross-sectional shape of the first fluid channel 110 may more accurately represent the actual shape of organic flow channels, such as airway lumens. This circular cross-sectional shape can improve the efficiency, effectiveness, and achievability of various organ functionality analyses, such as those pertaining to airflow and inhalation exposure studies. The circular-like cross-sectional shape can also facilitate laminar flow of fluid through the first channel, which can positively affect operation of the organ-on-chip apparatus 100.

In various embodiments, the interface 130 comprises a membrane and/or a porous structure. That is, the interface 130 may have pores that allow fluid exchange between the two channels 110, 120, and the endothelial and epithelial cells may reside on opposing sides of the interface 130 and may at least partially infiltrate the pores. In various embodiments, the ports of the interface 130 have a diameter between about 3 micrometers and about 5 micrometers. As used in this context only, the term "about" means plus or minus 0.5 micrometers.

In various embodiments, and with continued reference to FIGS. 3A and 3B, the first fluid channel 110 (e.g., the airway lumen) has a first diameter 111, the second fluid channel 120 (e.g., the vascular microchannel) has a second diameter 121, and the interface 130 has a span 131. In various embodiments, the second diameter 121 and the span 131 may be the same. In various embodiments, the first diameter 111 is between about 10% and about 50% greater than the second diameter 121. In various embodiments, the first diameter 111 is about 30% greater than the second diameter. As used in this context only, the term "about" means plus or minus 5%.

In various embodiments, and with reference to FIGS. 3A and 3B, opposing sidewalls of the first fluid channel 110 proximate the interface 130 have inflection points (e.g., inflection locations 112) where the curvature of the cross-sectional shape of the first fluid channel 110 changes from concave inward to concave outward. That is, the first fluid channel 110, having a circular cross-sectional shape, generally has a concave inward configuration in that a center of curvature of the shape of the first fluid channel is generally disposed within the first fluid channel 110. Between the inflection locations 112 and the interface 130, transition sections 113 (e.g., portions of opposing sidewalls) of the first fluid channel 110 are curved such that the respective centers of curvature 143 of the transition sections 113 are outside the first fluid channel (i.e., concave outward). In various embodiments, the opposing transition sections 113 define a neck 140 having a neck diameter 141. In various the neck diameter 141 is the smallest distance between the transition sections 113. The neck diameter 141, according to various embodiments, is less than the span 131 of the interface 130. That is, the neck diameter 141 is a first dimension of a tapered portion of the first fluid channel 110 and the span 131 of the interface 130 is a second dimension, parallel to the first dimension, which is larger than the first dimension.

In various embodiments, a radius of curvature 142 of the transition sections 113 of the first fluid channel 110 is between about ⅒ and ⅓ of the span 131 of the interface 130. In various embodiments, the radius of curvature 142 of the transition sections 113 of the first fluid channel 110 is about ⅕ of the span 131 of the interface 130. As used in this context only, the term "about" means plus or minus ¹⁄₂₀.

In various embodiments, the configuration of the apparatus having these relative dimensions and/or the inflection configuration is beneficial for recapitulation of pathophysiology, including but not limited to cilia synchrony of mucociliated epithelium. Further, as mentioned above, having the apparatus 100 configured with the relative dimensions described above may be important in order to accurately represent the actual shape of organic flow channels, such as airway lumens, which can improve the efficiency, effectiveness, and achievability of various organ functionality analyses, such as those pertaining to airflow and inhalation exposure studies, thus positively affecting operation of the organ-on-chip apparatus 100. Additionally, such a configuration may increase biological sample collection and ease of quantification. In one example, the first diameter is 1.33 millimeters, and the span 131 of the interface 130 and the second diameter 121 of the second fluid channel 120 are both 1.0 millimeter. Continuing the example, the radius of curvature 142 of the transition sections 113 may be 0.2 millimeters.

Figure 4:
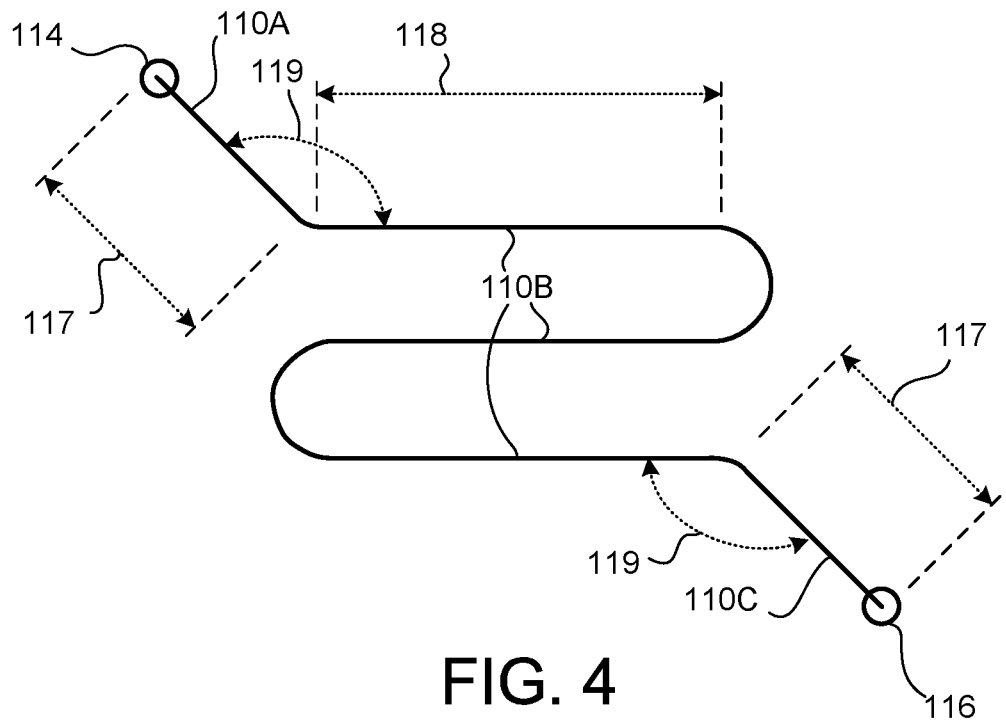
FIG. 4 is a schematic plan view showing a first longitudinal shape of a first fluid channel of an organ-on-chip apparatus, in accordance with various embodiments.
Figure 5:
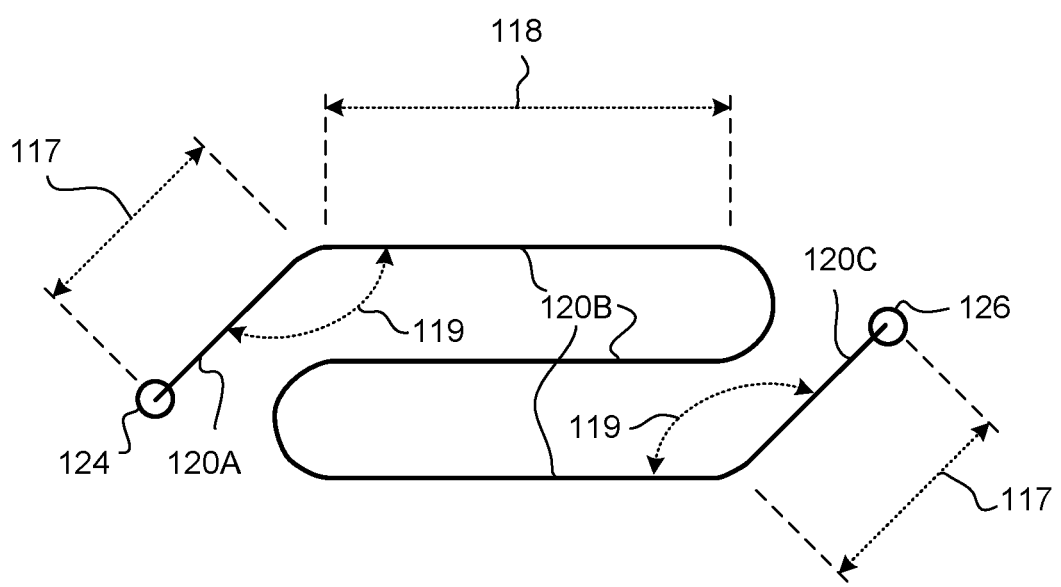
FIG. 5 is a schematic plan view showing a second longitudinal shape of a second fluid channel of an organ-on-chip apparatus, in accordance with various embodiments.

In various embodiments, and with reference to FIGS. 4 and 5, plan schematic views of the first fluid channel 110 and the second fluid channel 120 are provided, respectively. The first fluid channel 110 has a first inlet 114, a first inlet section 110A, a first body section 110B (i.e., the portion that overlaps with a corresponding portion 120B of the second fluid channel 120), a first outlet section 110C, and a first outlet 116, according to various embodiments. The second fluid channel 120 has a second inlet 124, a second inlet section 120A, a second body section 120B (i.e., the portion that overlaps with first body section 110B), a second outlet section 120C, and a second outlet 126. In various embodiments, the first inlet section 110A and the second inlet section 120A have the same longitudinal length 117. The respective inlet lengths may be important for establishing a desired laminar flow during operation of the apparatus. In various embodiments, the first outlet section 110C and the second outlet section 120C also have the same longitudinal length 117. In various embodiments, this longitudinal length 117 is about 50% of a longitudinal length of a straight-away portion 118 of the respective body sections 110B, 120B.

In various embodiments, the first and second inlet sections 110A, 120A may be angled relative to at least a beginning portion of the first and second body sections 110B, 120B, respectively. In various embodiments, this angle 119 is the same for both the first fluid channel 110 and the second fluid channel 120, though they may be oriented so that the respective inlet sections 110A, 120A extending in different directions. In various embodiments, this angle 119 is also that angle between the outlet sections 110C, 120C and respective ending portions of the first and second body sections 110B, 120B. That is, the angle 119 may be referred to as a uniform angle. This angle 119, according to various embodiments, is 135 degrees.

Figure 6:
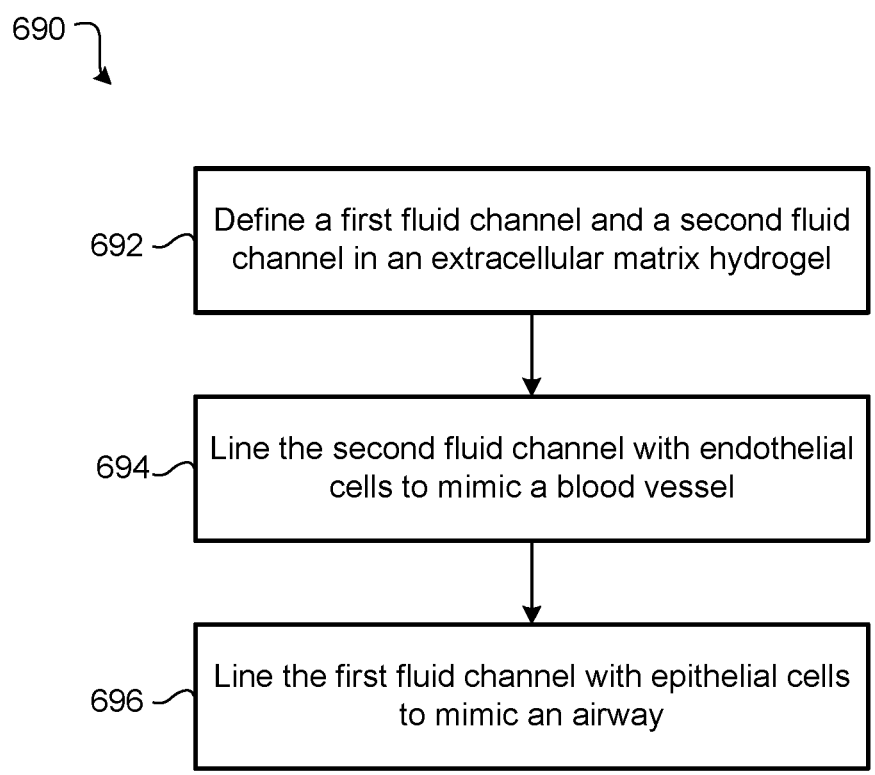
FIG. 6 is a schematic flow chart diagram of a method of manufacturing an organ-on-chip apparatus, in accordance with various embodiments.

In various embodiments, and with reference to FIG. 6, a method 690 of manufacturing an organ-on-chip apparatus is provided. The method 690 may include defining a first fluid channel and a second fluid channel in an extracellular matrix hydrogel at step 692, lining the second fluid channel with endothelial cells to mimic a blood vessel at step 694, and lining the first fluid channel with epithelial cells to mimic an airway at step 696.

In various embodiments, step 692 may include utilizing a "viscous fingering" method to generate the lumens/channels in collagen gel. Steps 694 and 696 may include forming a tight monolayer of corresponding cells to mimic the structure of airways and blood vessels in vitro in a reductionist manner. In various embodiments, as mentioned above, this method 690 includes generating an in vivo-like rounded airway lumen and the method 690 enables direct interaction of endothelium with underlying extracellular matrix material and/or a porous membrane as the interface. In various embodiments, the method 690 allows for incorporation of stromal cells in the extracellular matrix hydrogel.

The method 690 may further include oxygen-plasma-treating the defined channels to sterilize the device for cell culture and/or allowing stable extracellular interaction between the second fluid channel and the collagen hydrogel. In various embodiments, the method 690 may include, after the plasma treatment step, filling the second fluid channel with 3-6 mg/mL human collagen types I & IV (±other desired matrix proteins such as laminin, fibronectin, etc.) at or near the freezing point of water (e.g., 0 degrees Celsius). The method 690 may also include loading this material with human lung fibroblasts (healthy or diseased) at 0.5-3×10⁶ cells/ml. Immediately after filling the devices with the collagen solution, the method 690 may include allowing 100 μl of fibroblast culture medium, at or near 0 degrees Celsius, to pass through via a 200 μl-pipette tip inserted in the second inlet of the second fluid channel. This medium may be dispensed through the hydrogel solution via surface tension-based passive pumping. After collagen gelation by incubating for 30-45 minutes at 37° C. in a humidified incubator, the apparatus may be rinsed extensively with pre-warmed culture medium and stored in a cell culture incubator for an additional 18-24 hours.

The method 690 may further include seeding human small airway (bronchial, tracheal or nasal) epithelial cells (healthy or diseased) at representative density of 2.5-5×106 cells/mL on the top of the interface in epithelial cell culture medium and allowing these cells to attach and expand for 3-5 days before replacing the fluid in the airway channel with air to introduce an air-liquid interface (ALI). The epithelium may then be cultured for about 3-5 weeks to induce mucociliary differentiation under ALI. Subsequently, primary human lung microvascular endothelial cells (or any desired endothelial cell type; e.g., macrovascular, human umbilical vein endothelial cells [HUVECs], etc.) may be seeded in two phases at representative density of 4×106 cells/mL by flowing the cell suspension through the collagen gel lumen so that enough volume fills up the channel. In the first phase, the device will be incubated for 30 minutes at 37° C. in a humidified incubator in upright position. In the second phase, fresh endothelial cell suspension will be added into the hydrogel and the device will be incubated for an additional 30 minutes in an upside-down orientation. During both phases, endothelial culture medium will be used for seeding. The devices will next be connected to a peristaltic pump to create flow for 3 days to allow tight endothelial monolayer formation.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus

What is claimed is:

1. An organ-on-chip apparatus comprising:
   a first fluid channel, the interior of the first fluid channel lined with an extracellular matrix hydrogel;
   a second fluid channel, the interior of the second fluid channel lined with the extracellular matrix hydrogel, wherein respective portions of the first fluid channel and the second fluid channel extend parallel to and adjacent each other; and
   an interface disposed between the respective portions of the first fluid channel and the second fluid channel, wherein fluid exchange between the first fluid channel and the second fluid channel is via the interface,
   wherein the first fluid channel is an airway lumen and the second fluid channel is a vascular microchannel,
   wherein the airway lumen is further lined with at least one of alveolar, bronchiolar, bronchial tracheal, and nasal epithelial cells, wherein a gaseous fluid is configured to flow through the airway lumen,
   wherein the vascular microchannel is further lined with at least one of microvascular and lymphatic endothelial cells, wherein a liquid fluid is configured to flow through the vascular microchannel,
   wherein the airway lumen comprises a circular cross-sectional shape,
   wherein, in a cross-section normal to the flow of the gaseous fluid, each of two opposing sidewalls of the airway lumen proximate the interface comprise a center of curvature where the circular shape changes from concave inward to concave outward, wherein a distance between the two centers of curvature define a neck diameter parallel to the interface, and wherein the neck diameter is smaller than a span of the interface defined by a width of the interface parallel to the neck diameter.

2. The apparatus of claim 1, wherein a gaseous fluid is configured to flow through the airway lumen.

3. The apparatus of claim 1, wherein a liquid fluid is configured to flow through the vascular microchannel.

4. The apparatus of claim 1, wherein the interface comprises at least one of a membrane and a porous structure, wherein the at least one of the membrane and the porous structure comprises pores having a diameter between about 3 micrometers and 5 micrometers.

5. The apparatus of claim 1, wherein a first diameter of the airway lumen is about 30% greater than a second diameter of the vascular microchannel.

6. The apparatus of claim 1, wherein a first diameter of the airway lumen is greater than the span of the interface and a second diameter of the vascular microchannel is equal to the span of the interface.

7. The apparatus of claim 1, wherein transition sections of the airway lumen between each of the center of curvatures and the interface are concave outward, and wherein a radius of curvature of the transition sections of the airway lumen is ⅕ of the span of the interface.

8. The apparatus of claim 1, wherein:
the first fluid channel comprises a first inlet, a first inlet section, a first body section, a first outlet section, and a first outlet; and
the second fluid channel comprises a second inlet, a second inlet section, a second body section, a second outlet section, and a second outlet.

9. The apparatus of claim 8, wherein the first inlet section and the second inlet section have a same longitudinal length.

10. The apparatus of claim 9, wherein the first outlet section and the second outlet section also have the same longitudinal length.

11. The apparatus of claim 8, wherein a uniform angle is defined between:
the first inlet section and a first beginning portion of the first body section;
a first ending portion of the first body section and the first outlet section;
the second outlet section and a second beginning portion of the second body section; and
a second ending portion of the second body section and the second outlet section.

12. The apparatus of claim 11, wherein the uniform angle is about 135 degrees.

13. An organ-on-chip apparatus comprising:
an airway lumen lined with at least one of alveolar, bronchiolar, bronchial tracheal, and nasal epithelial cells, wherein a gaseous fluid is configured to flow through the airway lumen, wherein the airway lumen comprises a circular cross-sectional shape, and wherein the interior of the airway lumen is further lined with an extracellular matrix hydrogel;
a vascular microchannel lined with at least one of microvascular and lymphatic endothelial cells, wherein a liquid fluid is configured to flow through the vascular microchannel, wherein the interior of the vascular microchannel is further lined with the extracellular matrix hydrogel, wherein respective portions of the airway lumen and the vascular microchannel extend parallel to and adjacent each other; and
an interface disposed between the respective portions of the airway lumen and the vascular microchannel, wherein fluid exchange between the airway lumen and the vascular microchannel is via the interface, wherein the interface comprises at least one of a membrane and a porous structure,
wherein the airway lumen comprises a circular cross-sectional shape,
wherein, in a cross-section normal to the flow of the gaseous fluid, each of two opposing sidewalls of the airway lumen proximate the interface comprise a center of curvature where the circular shape changes from concave inward to concave outward,
wherein a distance between the two centers of curvature define a neck diameter parallel to the interface, and
wherein the neck diameter is smaller than a span of the interface defined by a width of the interface parallel to the neck diameter.

* * * * *